(12) United States Patent
Antelman

(10) Patent No.: US 6,669,966 B1
(45) Date of Patent: *Dec. 30, 2003

(54) COMPOSITIONS FOR FACILITATING SKIN GROWTH AND METHODS AND ARTICLES USING SAME

(75) Inventor: Marvin S. Antelman, Rehovot (IL)

(73) Assignee: Marantech Holding LLC, East Providence, RI (US)

(*) Notice: Subject to any disclaimer, the term of this patent is extended or adjusted under 35 U.S.C. 154(b) by 0 days.

This patent is subject to a terminal disclaimer.

(21) Appl. No.: 09/692,127

(22) Filed: Oct. 20, 2000

Related U.S. Application Data

(63) Continuation-in-part of application No. 09/552,172, filed on Apr. 18, 2000, now Pat. No. 6,258,385.
(60) Provisional application No. 60/174,793, filed on Jan. 6, 2000, provisional application No. 60/184,053, filed on Feb. 22, 2000, and provisional application No. 60/214,503, filed on Jun. 28, 2000.

(51) Int. Cl.$^7$ .......... A61K 33/34; A61K 9/00; A61K 31/60; A61K 33/00; A61K 35/78; A61K 47/00; A61L 15/00; A01N 25/00

(52) U.S. Cl. .......... 424/635; 424/405; 424/407; 424/443; 424/445; 424/446; 424/447; 424/489; 424/600; 424/613; 424/617; 424/639; 424/646; 424/647; 424/648; 424/653; 424/724; 424/725; 424/DIG. 6; 424/DIG. 13; 514/165; 514/772; 514/772.3; 514/788.1; 514/836; 514/904; 514/905; 514/925; 514/928; 514/950

(58) Field of Search .......... 424/600, 617, 424/618, 630, 635, 639, 646, 647, 648, 653, 405, 407, 443, 445, 446, 447, 489, 613, 724, 725, DIG. 6, DIG. 13; 514/165, 772, 772.3, 788.1, 836, 904, 905, 925, 928, 950

(56) References Cited

U.S. PATENT DOCUMENTS

| | | |
|---|---|---|
| 3,923,982 A | 12/1975 | Lamand et al. .......... 424/140 |
| 4,447,254 A | 5/1984 | Hughes et al. .......... 71/67 |
| 4,828,832 A | 5/1989 | De Cuellar et al. .......... 424/618 |
| 4,952,411 A | 8/1990 | Fox, Jr. et al. .......... 424/618 |
| 5,017,295 A | 5/1991 | Antelman .......... 210/764 |
| 5,073,382 A | 12/1991 | Antelman .......... 424/604 |
| 5,078,902 A | 1/1992 | Antelman .......... 210/764 |
| 5,089,275 A | 2/1992 | Antelman .......... 424/602 |
| 5,098,582 A | 3/1992 | Antelman .......... 210/759 |
| 5,211,855 A | 5/1993 | Antelman .......... 210/758 |
| 5,223,149 A | 6/1993 | Antelman .......... 210/764 |
| 5,334,588 A | 8/1994 | Fox, Jr. et al. .......... 514/171 |
| 5,336,416 A | 8/1994 | Antelman .......... 210/764 |
| 5,336,499 A | 8/1994 | Antelman .......... 424/405 |
| 5,492,754 A * | 2/1996 | Chen .......... 442/398 |
| 5,571,520 A | 11/1996 | Antelman .......... 424/405 |
| 5,612,019 A | 3/1997 | Gordon et al. .......... 424/9.32 |
| 5,676,977 A | 10/1997 | Antelman .......... 424/618 |
| 5,772,896 A | 6/1998 | Denkewicz, Jr. et al. .... 210/754 |
| 6,074,385 A * | 6/2000 | Klopotek .......... 606/27 |
| 6,228,491 B1 * | 5/2001 | Antelman .......... 428/372 |
| 6,258,385 B1 * | 7/2001 | Antelman .......... 424/618 |

FOREIGN PATENT DOCUMENTS

JP    2000060976    2/2000

OTHER PUBLICATIONS

Dorland et al., *Dorland's Illustrated Medical Dictionary*, Philadelphia: W.B. Saunders Company, 1994, 28$^{th}$ Edition, p. 351, 759, and 760.
Gennaro, A., Remington's Pharmaceutical Sciences, Easton, PA: Mack Publishing Company, 1985, 17$^{th}$ Edition, p. 1573–1575, 1585–1594, and 1601.
Antelman, Marvin S.; "Silver (II,III) Disinfectants"; *Soap/Cosmetics/Chemical Specialties*, Mar. 1994, pp. 52–59.
Antelman, Marvin S.; *Abstracts of the American Chemical Society*; 1992(203).
Antelman, Marvin S.; "Anti–Pathogenic Multivalent Silver Molecular Semiconductors"; *Precious Metals*; 1992(16); pp. 141–149.
Antelman, Marvin S.; "Multivalent Silver Bacterides"; *Precious Metals*; 1992(16); pp. 151–163.
Fung, Man C. and Bowen, Debra L.; "Silver Products for Medical Indications: Risk–Benefit Assessment", *Clinical Toxicology*, 1996, pp. 119–126.

* cited by examiner

*Primary Examiner*—S. Mark Clardy
*Assistant Examiner*—Frank Choi
(74) *Attorney, Agent, or Firm*—Pennie & Edmonds LLP

(57) ABSTRACT

Skin-growth-enhancing compounds and compositions including a therapeutically effective amount of at least one electron active compound, or a pharmaceutically acceptable derivative thereof, that has at least two polyvalent cations, at least one of which has a first valence state and at least one of which has a second, different valence state. Preferred compounds include Bi(III,V) oxide, Co(II,III) oxide, Cu(I, III) oxide, Fe(II,III) oxide, Mn(II,III) oxide, and Pr(III,IV) oxide, and Ag(I,III) oxide, or a combination thereof. These compounds may be in a crystalline state having metallic cations of two different valences, or electronic states, in the inorganic crystal. Also included are articles containing such compositions, such as wound dressings, and methods for facilitating or enhancing skin growth using these compounds, compositions, and articles, such as for the treatment or management of burns or skin grafts.

25 Claims, No Drawings

COMPOSITIONS FOR FACILITATING SKIN GROWTH AND METHODS AND ARTICLES USING SAME

CROSS-REFERENCE TO RELATED APPLICATION

This application is a continuation-in-part of application Ser. No. 09/552,172, filed Apr. 18, 2000, now U.S. Pat. No. 6,258,385, and claims the benefit of Provisional Application Nos. 60/174,793, filed Jan. 6, 2000, 60/184,053, filed Feb. 22, 2000, and 60/214,503, filed Jun. 28, 2000.

FIELD OF THE INVENTION

The invention relates to skin-growth-enhancing compositions including certain compounds having polyvalent cations in their crystal lattices, particularly certain inorganic metal oxides. Articles and methods of facilitating or enhancing skin growth to treat or manage certain conditions, such as burn therapy or skin grafts, using such skin growth compositions are included in the invention.

BACKGROUND OF THE INVENTION

Animal and mammalian skin, in particular, human skin, is a multifunctional organ. Not only does the skin provide an external covering to protect the body, but it also performs several specialized functions, such as breathing, perspiring, sensory information processing, and oil production. Oil production, essential to the protective features of the skin, works when an oily substance known as seburn is released from the sebaceous glands, which are large glands located at the base of a hair follicle. This permits the skin to moisturize and waterproof itself, thereby protecting itself from the environment.

The skin is the most environmentally-stressed organ in mammals, particularly in humans. The skin is subjected to toxic chemicals and hostile environments, as well as being the only organ directly exposed to Ultraviolet ("UV") light in the presence of oxygen. Lengthy exposure of the skin to UV light typically damages the skin, resulting, in sunburn, photoaging, carcinogenesis, and other related skin disorders.

In particular, human skin is a composite material of the epidermis and the dermis. The topmost part of the epidermis is the stratum corneum. This layer is the stiffest layer of the skin, as well as the one most affected by the surrounding environment. Below the stratum corneum is the internal portion of the epidermis. Below the epidermis, the topmost layer of the dermis is the papillary dermis, which is made of relatively loose connective tissues that define the microrelief of the skin. The reticular dermis, disposed beneath the papillary dermis, is tight, connective tissue that is spatially organized. The reticular dermis is also associated with coarse wrinkles. At the bottom of the dermis lies the subcutaneous layer.

The principal functions of the skin include protection, excretion, secretion, absorption, thermoregulation, pigmentogenesis, accumulation, sensory perception, and regulation of immunological processes. These functions are detrimentally affected by the structural changes in the skin due to aging and excessive sun exposure. The physiological changes associated with skin aging include impairment of the barrier function and decreased turnover of epidermal cells, for example.

The mechanical properties of the skin, such as elasticity, are believed to be controlled by the density and geometry of the network of collagen and elastic fiber tissue therein. Damaged collagen and elastin lose their contractile properties, resulting in skin wrinkling and skin surface roughness. As the skin ages or becomes unhealthy, it acquires sags, stretch marks, burns, bruises or wrinkles, it roughens, and it has reduced ability to synthesize Vitamin D. Aged skin also becomes thinner and has a flattened dermoepidermal interface because of the alterations in collagen, elastin, and glycosaminoglycans.

UV light exposure in the presence of oxygen results in the undesirable creation of free radicals, which is believed to lead to various skin disorders, diseases, or conditions. In the skin, these free radicals frequently trigger the release of inflammatory mediators, commonly manifested as sun burn; cytoskeletal alterations, breaking down the collagen in the skin; and may also result in structural DNA changes, such as DNA strand breaks and dimer formation. The body attempts to neutralize the free radicals generated by UV light through the use of antioxidants. Antioxidants are commonly found in two forms—enzymatic and non-enzymatic.

Various ingredients have been used alone or in certain combinations to form pharmaceuticals designed to prevent and treat certain cellular, skin, and other conditions, such as burns. Although a variety of compositions and methods for treating various skin conditions are presently available to those of ordinary skill in the art, the treatments are often not completely effective and often involve adverse effects, such as overdrying of the skin. Furthermore, some existing treatments simply address the symptoms and fail to treat the underlying condition, as well as helping to reduce the incidence of remission or the appearance of recurring or new disorders.

Multivalent silver molecules have also been disclosed for various uses, as they are reported to be non-toxic to animals and humans. M. Antelman, "Anti-Pathogenic Multivalent Silver Molecular Semiconductors," *Precious Metals*, vol. 16:141–149 (1992); M. Antelman, "Multivalent Silver Bactericides," *Precious Metals*, vol. 16:151–163 (1992). For example, tetrasilver tetroxide activated with an oxidizing agent is disclosed for use in bactericidal, fungicidal, and algicidal use, such as in municipal and industrial water treatment applications and for the treatment of AIDS.

A variety of sources also report the use of certain divalent silver compounds for water treatment, as well as the use of such compounds, typically in combination with certain oxidizing agents, metals, or other compounds, as disinfectants, bactericides, algicides, and fungicides. One source also reports a single in vitro study of the use of such compounds for the treatment of AIDS. These sources include M. Antelman, "Silver (II, III) Disinfectants," *Soap/Cosmetics/Chemical Specialties*, pp. 52–59 (Mar., 1994), and U.S. Pat. Nos. 5,017,295; 5,073,382; 5,078,902; 5,089,275; 5,098,582; 5,211,855; 5,223,149; 5,336,416; and 5,772,896.

U.S. Pat. No. 5,336,499 discloses tetrasilver tetroxide and persulfate compositions having certain in vitro anti-pathogenic properties, i.e., bactericidal, fungicidal, viricidal, and algicidal, in certain concentrations as low as 0.3 ppm, particularly in nutrient broth cultures. The persulfate or another oxidizing agent is required to activate the tetroxide crystals. Also disclosed are: an in vitro study regarding the inhibition of yeast growth in nutrient broth and the formulation of a gynecological cream and douche based on these results, and a report of an in vitro AIDS test with the compositions indicating total suppression of the virus at 18.0 ppm.

U.S. Pat. No. 5,571,520 discloses the use of molecular crystals of tetrasilver tetroxide, particularly with oxidizing agents to enhance the efficiency of such devices, for killing pathogenic microorganisms, such as staph infections. Amounts of 10 ppm sodium persulfate as an oxidizing agent were used with certain amounts of silver tetroxide in the reported in vitro testing. One human study involved in vivo curing of a gynecological yeast infection with 10 ppm of the silver tetroxide and 40 ppm sodium persulfate. Other in vivo topical studies report in conclusory fashion the cure of a single case of athlete's foot with a solution of 100 ppm of the composition and the cure of a single case of toenail fungus with a 25% suspension of the composition.

U.S. Pat. No. 5,676,977 discloses intravenously injected tetrasilver tetroxide crystals used for destroying the AIDS virus, AIDS synergistic pathogens, and immunity suppressing moieties (ISM) in humans. The crystals were formulated for a single injection at about 40 ppm of human blood. This reference also discloses the compositions cause hepatomegaly, also known as enlarged liver, albeit with no reported loss of liver function.

The aforementioned references report detailed descriptions of the mechanism via which the multivalent silver molecular crystal devices were believed to operate. A discussion of such results and concepts was presented at a Seminar entitled "Incurable Diseases Update" (Weizmann Institute of Science, Rehovot, Israel, Feb. 11, 1998). The title of this presentation was "Beyond Antibiotics, Non Toxic Disinfectants and Tetrasil™ (a composition including tetrasilver tetroxide)." In this article, it was reported that the effects of the electron transfer involved with respect to the tetroxide, rendered it a more powerful germicide than other silver entities. Other patents cover multivalent silver antimicrobial compositions, e.g., U.S. Pat. Nos. 5,017,295 for Ag(II) and 5,223,149 for Ag (III). These are stronger antimicrobial agents than Ag (I) compounds, but they pale by comparison to tetrasilver tetroxide.

Likewise, colloidal silver that derives its germicidal properties from trace silver (I) ions it generates in various environments is also less effective. Accordingly, the oligodynamic properties of these entities may be summarized as follows, which is referred to as the Horsfal series:

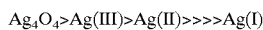

$Ag_4O_4 > Ag(III) > Ag(II) >>>> Ag(I)$

Another property of the tetrasilver tetroxide is that it does not stain organic matter such as skin in like manner as Ag(I) compounds do. In addition, it is light stable.

Further, synthetic routes for making Bi(III,V) oxide are detailed and reviewed in *Gmelins Handbuch DerAnorganischen Chemie*, vol. 16:642 (1964). Also, Co(II,III) oxide, Fe(II,III) oxide, Mn(II,III) oxide, and Pr(III,IV) oxide can all be found in nature. These five multivalent metal oxides are also all available commercially.

Certain skin conditions, such as burns, skin cancer, and skin grafts, however, require the growth or regrowth of damaged or eradicated tissue. Burns to skin are caused by thermal, chemical, or electrical contact, which results in, for example, protein denaturation, burn wound edema, loss of intravascular fluid volume due to increase vascular permeability, and combinations thereof. Systemic effects, for example, hypovolemic shock, infection, respiratory tract injury, or a combination thereof, pose a greater threat to the life of the victim that do the above-noted local effects.

In spontaneous burn wound healing, dead tissue sloughs off as new epithelium begins to cover the injured area. In superficial burns, regeneration or growth of skin tissue occurs rapidly from, for example, uninjured epidermal elements, hair follicles, and sweat glands. Minimal scarring typically results unless infection occurs during the healing process. With deep burns, i.e., destruction of the epidermis and much of the dermis, reepithelialization typically begins from the edges of the wound or from the scattered remains of integument. The process is typically slow, and excessive granulation tissue often forms before being covered by new epithelium. Such wounds generally contract and develop into disfiguring or disabling scars unless treated promptly by, for example, skin grafting. Unfortunately, some skin grafts are rejected by the host's body in the absence of immune suppression treatment, which adds additional expense to the treatment and often creates additional adverse effects in the patient.

The severity of a burn is judged by the quantity of tissue involved. This quantity is represented by the percentage of body surface area (% BSA) burned and by the depth of the burn. A conventional classification of burns by severity is: small burn, or less than 15% BSA; moderate burn, or 15% to 49% BSA; large burn, or 50% to 69% BSA; and massive burn, or greater than 70% BSA.

The depth of a burn may be described as a first, second, or third degree burn. First degree burns are red, very sensitive to the touch, and usually moist. Blisters typically do not form and the surface markedly and widely blanches under light pressure. Second degree burns may or may not have blisters, but the wound base is sensitive to touch and may blanch to pressure. Third degree burns may, but generally do not, present blisters. The skin surface may be white and pliable when pressure is applied, or it may be black, charred, and leathery. Third degree burns may be pale in color and even mistaken for normal skin, but the subdermal vessels do not blanch to pressure. The wound may alternatively be bright red, due to fixed hemoglobin in the subdermal region. The third degree burns are generally anasthetic or hypoesthetic, with hair being easily pulled from the follicles. Often, the distinction between deep second and third degree burns can be made only after 3 to 5 days of observation.

U.S. Pat. No. 4,828,832 to De Cuellar et al. discloses metallic silver particles and an oxidizing agent, such as benzoyl peroxide, dispersed in a carrier for application to a skin lesion, such as for the treatment of burns.

The above-noted compositions are not believed to have suitable efficacy in treating or managing conditions that require skin growth, such as the treatment or management of burns.

Thus, it is desired to find skin-growth-enhancing pharmaceutical compositions and methods for facilitating or enhancing skin growth to treat or manage one or more dermatological conditions. It is also desired to facilitate or enhance the rate of skin growth while avoiding adverse effects present when administering certain conventional treatments or skin replacement.

SUMMARY OF THE INVENTION

The invention relates to methods for facilitating or enhancing skin growth of a patient's skin, by administering at least one electron active compound, or a pharmaceutically acceptable derivative thereof, that has at least two polyvalent cations, at least one of which has a first valence state and at least one of which has a second different valence state, to treat or manage the condition, or a symptom thereof, in an amount and for a period of time which is therapeutically effective to facilitate or enhance skin growth.

In one embodiment, the patient is a mammal and the therapeutically effective amount of the electron active metal oxide compound(s) administered is from about 1 ppm to 500,000 ppm. In another embodiment, the therapeutically effective amount is from about 50 ppm to 100,000 ppm. In yet another embodiment, the mammal is a human and the at least one electron active metal oxide compound is administered topically, parenterally, or transdermally.

In one embodiment, the method further includes administering at least one additional different therapeutic agent present in an amount sufficient to facilitate or enhance the treatment or management of the condition. It is possible to administer the at least one additional therapeutic agent concurrently with the at least one electron active metal oxide compound, although in other embodiments administration may be sequential in either order.

Preferably, the at least one electron active compound includes a metal oxide. In one embodiment, the electron active compound includes at least one of Bi(III,V) oxide, Co(II,III) oxide, Cu(I,III) oxide, Fe(II,III) oxide, Mn(II,III) oxide, or Pr(III,IV) oxide, or a pharmaceutically acceptable derivative thereof.

It is also possible to combine the at least one electron active compound with a carrier medium before administration to the patient. In one preferred embodiment, the carrier medium includes petroleum jelly. In some embodiments, no carrier is required, and the composition is administered in the form of a powder, or a plurality of powder crystals or granules. In one topical embodiment, the carrier medium includes a thixotropic agent sufficient to increase adherence of the composition to the skin without excessive runoff. The at least one electron active compound may be applied to the skin at a dosage level of about 10 mg to 500 mg per $cm^2$ of skin surface. Preferably, the therapeutically effective amount administered is insufficient to cause adverse effects.

Preferably, the facilitating or enhancing of skin growth comprises the treatment or management of a burn or skin graft. In one embodiment, a pathogen is killed concurrently with the treatment or management of a burn or skin graft. Alternatively, the growth of a pathogen is halted, diminished, or inhibited concurrently with the treatment or management of a burn or skin graft.

The present invention also relates to skin-growth-enhancing compositions that include at least one electron active compound, or a pharmaceutically acceptable derivative thereof, that has at least two polyvalent cations, at least one of which has a first valence state and at least one of which has a second, different valence state, in an amount and for a period of time which is therapeutically effective to facilitate or enhance skin growth. Advantageously, the pharmaceutical composition may have antipathogenic efficacy. Preferably, the at least one electron active compound includes a metal oxide. In one embodiment, the metal oxide includes at least one of bismuth, cobalt, copper, iron, manganese, praseodymium, or a combination thereof. Preferably, in that embodiment, the metal oxide includes at least one of Bi(III,V) oxide, Co(II,III) oxide, Cu(I,III) oxide, Fe(II,III) oxide, Mn(II,III) oxide, Pr(III,IV) oxide, Ag(I,III) oxide, or a combination thereof. Alternately, the pharmaceutical composition does not include tetrasilver tetroxide. In another alternate embodiment, the pharmaceutical composition does not include tricobalt tetroxide. In one embodiment, the pharmaceutical composition may include at least two different electron active compounds. In another embodiment, the compound may be in powder, powder crystal, or granular form.

In a preferred embodiment, the first valence and the second valence of the at least two polyvalent cations differ by at least 1, preferably by 1 or 2. In another preferred embodiment, the first valence and the second valence of the at least two polyvalent cations differ by more than 2. Advantageously, the electron active compound has at least one polyvalent cation which has an $EMF^{ox}$ of at least about +0.1 Volts.

In one embodiment, the amount of the at least one electron active compound is present in an amount from about 1 ppm to 500,000 ppm, based on the weight of the composition. If desired, the pharmaceutical composition can include a pharmaceutically acceptable carrier. In one embodiment, the carrier includes a petroleum jelly. In one preferred embodiment, the carrier medium is adapted for topical administration comprises a thixotropic agent sufficient to increase adherence of the composition to skin without excessive runoff. Optionally, the composition can also include an oxidizing agent, preferably present in an amount sufficient to enhance the efficacy of the active compound but insufficient to cause skin irritation. Preferably, the oxidizing agent includes a peroxy acid salt of a persulfate.

The invention also relates to articles including the skin-growth-enhancing compounds or compositions according to the invention. One preferred embodiment includes a wound dressing including the at least one compound or composition of the invention. In a more preferred embodiment, the wound dressing includes an adhesive-containing bandage, a cotton roll bandage, or a gellable polymer. The gellable polymer may be any polymer, or combination thereof, available to those of ordinary skill in the art, that has sufficiently low viscosity to flow onto a skin area requiring treatment or management and that subsequently thickens sufficiently upon application to a wound so as to remain substantially affixed to the wound for a time sufficient to provide treatment or management to the skin condition. The thickening may occur, for example, by exposure to air, moisture in the air or wound, by combination of two polymers directly on the afflicted skin area, or due to heat from the afflicted skin area.

DEFINITIONS

Some of the terms used in connection with the invention can be defined as follows:

The term "condition," as used herein, should be understood to refer to a traditionally identified disease, as well as a disorder, an affliction, or an ailment, particularly including those noted herein. In particular, as used herein the term "condition" includes burns, wounds, or sores, or a symptom thereof, such as where treatment or management thereof requires skin growth. In one embodiment, condition refers to burns or wounds other than mere sores.

The terms "prevent," "preventing," and "prevention," as used herein, refer to stopping or hindering a condition, symptom, or pathogen causing a condition, in a patient who is at risk of suffering from such a condition. This also includes reducing the frequency or severity, or both, of the occurrence of such conditions or one or more symptoms thereof.

The terms "manage," "managing," and "management," as used herein, includes controlling those conditions which cannot be cured completely, reducing the time of affliction of such conditions, and the like. Preferably, the compositions prevent, treat, or manage such conditions without superficially discoloring the skin, i.e., no discoloration to the naked eye. In one embodiment, the invention relates to the treatment or management, while in another embodiment the invention relates to the prevention, of the diseases or conditions disclosed and claimed herein. The terms also include the use of the compounds or compositions of the invention to facilitate the halting, diminishing, or inhibiting of the growth or proliferation of pathogens that may accentuate, amplify, exacerbate, or cause, either directly or indirectly, a condition and/or a symptom thereof.

The term "patient" as used herein refers to animals, particularly to mammals. In one preferred embodiment, the term patient refers to humans.

The terms "adverse effects," "adverse side effects," and "side effects," as used herein, include, but are not limited to, cardiac arrhythmia, cardiac conduction disturbances, appetite stimulation, weight gain, sedation, gastrointestinal distress, headache, dry mouth, constipation, diarrhea, drug-drug interactions, superficial discoloration of the skin, dry skin, hepatomegaly, fever, fatigue, and the like. The term "cardiac arrhythmia" includes, but is not limited to, ventricular tachyrhythmia, torsades de pointes, $Q_T$ prolongation, and ventricular fibrillation.

The phrase "therapeutically effective amount" when used herein in connection with the compositions and methods of the invention, means that amount of electron active metal oxide compound(s) or composition(s), or a derivative thereof, which, alone or in combination with other drugs, provides a therapeutic benefit in the treatment or management of a condition. In one embodiment, the effective amount is one or more metal oxide compounds or compositions as the sole active ingredient. Different therapeutically effective amounts may be applicable for each condition, as will be readily known or determined by those of ordinary skill in the art.

The term "substantially free" means less than about 10 weight percent, preferably less than about 5 weight percent, more preferably less than about 1 weight percent, and most preferably less than about 0.1 weight percent. For example, a composition may be substantially free of added oxidizing agent or of added persulfate according to the invention.

The term "about," as used herein, should generally be understood to refer to both numbers in a range of numerals. Moreover, all numerical ranges herein should be understood to include each whole integer within the range.

The term "substantial," as used herein, means at least about 75%, preferably at least about 90%, more preferably at least about 95%, most preferably at least about 99%.

The term "valence state," as used herein, should be understood to refer to the charge on a given ion or to the charge that may be assigned to a given ion based on its electronic state.

The term "wound," as used herein, should be understood to refer to a cut, laceration, abrasion, puncture or the like, especially in or on the skin.

The terms "inhibit," "inhibiting," or "inhibits," as used herein when referring to growth of an item, should be understood to refer to the act of stopping that growth, whether permanently or temporarily, or of reducing the rate of that growth, either permanently or temporarily.

DETAILED DESCRIPTION OF THE PREFERRED EMBODIMENTS

The tetrasilver tetroxide compounds mentioned in the background are one type of electron active compound having multivalent cations in its crystal lattice. Various additional electron active compounds have now also been identified, as well as methods for making and using the same for treating various pathogenic and non-pathogenic conditions or disorders. It has now been discovered that such electron active compounds, and compositions, beneficially enhance or facilitate the growth of skin. Thus, the compounds, compositions, and methods and articles using same, are advantageously used to treat or manage various conditions that require rapid soft tissue growth, such as burn therapy and skin grafts. The compounds and compositions of the invention can increase the rate at which soft tissue grows, or heals, compared to the ordinary rate in the absence of the invention. It is also believed that the compounds and compositions of the invention heal burns and other such conditions more rapidly and more comprehensively than conventional burn treatments, such as silver nitrate, silver sulfadiazine, and monovalent silver oxide ($Ag_2O$).

The electron active compounds of the present invention are believed to have unique crystal structures in that, in the case of the metal oxides, there are generally atoms of the same element in the crystal that have at least two different valences, typically at least one lower-valent metal cation and at least one higher-valent metal cation, for example, such as Co(II) and Co(III), respectively. Exemplary electron active metal oxide compounds according to the invention include, but are not limited to, Ag(I,III), Co(II,III), Pr(III,IV), Bi(III, V), Fe(II,III), Mn(II,III), and Cu(I,III) oxides. As discussed below, pharmaceutical compositions including one or more of such oxide compounds are useful for treating various conditions. The composition of such exemplary electron active metal oxides is shown in tabular form below:

| e | Formula | Metal cations | Lower-valent ion | # | Higher-valent ion | # |
|---|---------|---------------|------------------|---|-------------------|---|
| 2 | $Ag_4O_4$ | Ag(I,III) | $Ag^+$ | 2 | $Ag^{+3}$ | 2 |
| 1 | $Co_3O_4$ | Co(II,III) | $Co^{+2}$ | 1 | $Co^{+3}$ | 2 |
| 2 | $Pr_6O_{11}$ | Pr(III,IV) | $Pr^{+3}$ | 2 | $Pr^{+4}$ | 4 |
| 2 | $Bi_2O_4$ | Bi(III,V) | $Bi^{+3}$ | 1 | $Bi^{+5}$ | 1 |
| 1 | $Fe_3O_4$ | Fe(II,III) | $Fe^{+2}$ | 1 | $Fe^{+3}$ | 2 |
| 1 | $Mn_3O_4$ | Mn(II,III) | $Mn^{+2}$ | 1 | $Mn^{+3}$ | 2 |
| 2 | $Cu_4O_4$ | Cu(I,III) | $Cu^+$ | 2 | $Cu^{+3}$ | 2 | e-total number of electrons believed to be exchanged; #-number of particular ion type per formula unit.

Without being bound to theory, it is believed that the electron active compounds operate against pathogens by transferring electrons between their lower-valent ions and their higher-valent ions in the crystal, thereby contributing to the death of pathogens by traversing their cell membrane surface. It would seem that this, in effect, "electrocutes" the pathogens. While these compounds have also been discovered to be suitable for use in the prevention, treatment, and management of other non-pathogenic conditions and disorders, such as autoimmune disorders, circulatory disorders, neurological disorders, and the like, the mechanism by which such conditions or disorders are prevented, treated, or managed has not yet been fully understood. In any event, the electrons in pathogens are believed to be perturbed from their balanced crystals by such labile groups as NH, $NH_2$, S—S, and SH, which can be present, for example, in a pathogen cell membrane. It is believed, however, that normal cells will not be significantly affected because they do not proliferate rapidly enough to expose these labile bonds sufficiently for the bonds to be substantially affected.

The crystals in the electron active compounds are not believed to be disturbed unless more stable complexes are formed with ligands, for example, such as those comprising a pathogen cell membrane surface in a dynamic state. Indeed, the end result of electron transfer, which is a redox reaction, results in the lower-valent metal ions being oxidized to one valence state higher and the higher-valent metal ions being reduced to one valence state lower. In one embodiment, the oxidation of the lower-valent metal ions and the reduction of the higher-valent metal ions both result in ions having the same oxidation state. Examples of such an embodiment occur when the valence difference between the metal ions in the electron active molecular crystal is 2 and such examples include, but are not limited to, Ag(I,III), Bi(III,V), and Cu(I,III) oxides. In another embodiment, the oxidation of the lower-valent metal ions and the reduction of the higher-valent metal ions ?result in ions having opposite oxidation states (e.g., ions with a +2 valence state are oxidized to +3, while the ions with a +3 valence state are reduced to +2). Examples of such an embodiment occur when the valence difference between the metal ions in the electron active molecular crystal is 1 and such examples include, but are not limited to, Co(II,III), Fe(II,III), Mn(II, III), and Pr(III,IV) oxides.

The metal ion of certain electron active compounds may exhibit a distinct affinity for certain elements of ligands, for example, such as sulfur, oxygen, or nitrogen, particularly when present in a pathogen's cell membrane. In many cases, the metal ion will not merely bind to these elements, but will actually form chelate complexes with their ligands. The classic example of this is Ag(I,III) oxide, the monovalent silver ion of which has an affinity for sulfur and nitrogen and the oxidized/reduced divalent ion of which forms chelate complexes with, for example, mercapto or amino groups. Thus, the electron active compound attraction for the cell membrane surfaces, for example, of pathogens, is believed to be driven by powerful electrostatic forces.

Without being bound by theory, the electron exchange may be depicted, for example, by the following series of redox half reactions:

| metal(I,III) oxides | metal(II,III) oxides | metal(III,IV) oxides | metal(III,V) oxides |
|---|---|---|---|
| $Ag^+ - e = Ag^{+2}$ | $Co^{+2} - e = Co^{+3}$ | $Pr^{+3} - e = Pr^{+4}$ | $Bi^{+3} - e = Bi^{+4}$ |
| $Ag^{+3} + e = Ag^{+2}$ | $Co^{+3} + e = Co^{+2}$ | $Pr^{+4} + e = Pr^{+3}$ | $Bi^{+5} + e = Bi^{+4}$ |
| $Cu^+ - e = Cu^{+2}$ | $Fe^{+2} - e = Fe^{+3}$ | | |
| $Cu^{+3} + e = Cu^{+2}$ | $Fe^{+3} + e = Fe^{+2}$ | | |
| | $Mn^{+2} - e = Mn^{+3}$ | | |
| | $Mn^{+3} + e = Mn^{+2}$ | | |

For each redox reaction, there is believed to be an electromotive force, which is the voltage potential when oxidizing the higher-valent ion in the metal oxide crystal. This is denoted herein as $EMF^{OX}$. In addition to the electromotive force of oxidation, there is believed to be an associated reduction reaction involving the lower-valent ion in the metal oxide crystal. This reduction reaction may be represented simply, as tabulated above, or may represent the interaction with, for example, a ligand present on a pathogen cell membrane surface, such as one containing sulfur or nitrogen. Associated with the reduction reaction is another electromotive force, or voltage potential when reducing the lower-valent ion. This is denoted herein as $EMF^{RE}$.

When the metal ions of the electron active metal oxide interact with, for example, a sulfur-containing ligand, the affinity of the metal ion for sulfur affects $EMF^{RE}$. The stability of a particular metal sulfide is an approximation of the affinity of a metal ion for sulfur. The following approximate association constants for sulfides indicate the trend in relative affinity of each metal ion for sulfur:

| | |
|---|---|
| Ag(I) | 49 |
| Cu(I) | 47 |
| Co(II) | 26 |
| Fe(II) | 19 |
| Mn(II) | 15 |

In general, the more stable the compound, the more negative its reduction potential in the reduction reaction, for example, in the case of elemental silver:

$$2Ag + S^{-2} - 2e \rightarrow Ag_2S \quad EMF^{RE} = -0.66$$

In the case of tetrasilver tetroxide, there is a reduction reaction where Ag(I) is oxidized and an oxidation reaction where Ag(III) is reduced, as follows:

$$Ag^+ - e + S^{-2} - e \rightarrow AgS \quad EMF^{RE} = -0.90$$

$$Ag^{+3} - e \rightarrow Ag^{+2} \quad EMF^{OX} = +2.02$$

The voltage that is discharged from a redox reaction of the electron active metal oxides of the present invention, which voltage is denoted herein as the "electrocution voltage," is the combination of the oxidation and reduction potentials (i.e., $EMF^{OX} - EMF^{RE}$). In the case of tetrasilver tetroxide, the "electrocution voltage" is 2.92 volts. The oxidation potentials, $EMF^{OX}$, of exemplary metal oxides according to the present invention are tabulated below:

| Formula | Metal cations | $EMF^{OX}$ |
|---|---|---|
| $Ag_4O_4$ | Ag(I,III) | 2.02 |
| $Co_3O_4$ | Co(II,III) | 1.81 |
| $Pr_6O_{11}$ | Pr(III,IV) | 2.86 |
| $Bi_2O_4$ | Bi(III,V) | 1.59 |
| $Fe_3O_4$ | Fe(II,III) | 0.77 |
| $Mn_3O_4$ | Mn(II,III) | 1.54 |
| $Cu_4O_4$ | Cu(I,III) | 1.80 |

As noted from the above table, praseodymium-, cobalt-, and copper- based oxides are believed to be stronger antipathogenic agents or to form better pharmaceutical compositions than manganese-, bismuth-, and iron- based oxides, and in one embodiment they are preferred for this reason. Nevertheless, in certain cases, iron exhibits stronger antipathogenic characteristics, particularly antimicrobial characteristics, compared to manganese.

Another factor, however, particularly in antipathogenic or antimicrobial efficacy, can be the sulfur/nitrogen composition, for example, of cell membranes. For example, *Staphylococcus aureus* bacteria, in a culture having a cell density of 30,000 CFU/mL, exhibit significant mortality from exposure to 100 ppm of Bi(III,V) oxide for about 10 minutes, but no significant mortality from exposure to the same concentrations of Fe(II,III) and Mn(II,III) oxides for the same contact time. This result might be explained by the far greater stability of bismuth(III) sulfide, and thus the far greater affinity of bismuth(III) for sulfur, than either of the iron(II) or manganese(II) analogs.

The electron active metal oxide compounds and compositions of the present invention may be used in any form which sufficiently retains their antipathogenic character, or other non-pathogenic ability, to prevent, treat, or manage one or more of the conditions noted herein.

These compounds or compositions may be used as antipathogenic agents, such as antimicrobial, antibacterial, antiviral, or anti-algal agents, or a combination thereof. In another embodiment, the compounds or compositions may be used for preventing, treating, and/or managing various conditions that are non-pathogenic. For example, non-pathogenic conditions are believed to include certain autoimmune disorders, neurological disorders, and circulatory disorders. While the exact mechanism of the activity of such compounds or compositions is not described herein, nonetheless, suitable prevention, treatment, and/or management of such non-pathogenic conditions may be obtained by administering the compounds or compositions of the invention as described herein and as will be readily apparent to one of ordinary skill in the art.

The compositions and methods of the invention advantageously prevent, treat, or manage dermatological diseases or conditions. The conditions against which the electron active compounds, such as metal oxides, of the present invention have utility include, but are not limited to, Madura foot, actinomycosis, oral actinomycosis, anthrax, food poisoning, botulism, wound infections, pseudomembranous colitis, colitis, gas gangrene, gangrene, tetanus, diphtheria, pharyngeal diphtheria, pleomorphic laryngeal diphtheria, cutaneous diphtheria, endocarditis, bacteremia, urinary tract infections, listerosis, meningitis, miscarriage, narcodiosis, acne, skin lesions, abscesses, toxic shock syndrome, prosthesis contamination, dental caries, plaque, gum disease, gingivitis, subacute endocarditis, bacterial pneumonia, otitis, sinusitis, cat scratch fever, septicemia, abdominal and pelvic abscesses, Oroya fever, systemic Oroya fever, verruga peruana, cutaneous verruga peruana, whooping cough, Lyme disease, epidemic relapsing fever, brucellosis, granuloma inguinale granulomatic, donovanosis, gastroenteritis, nosocomial infections, tularemia, bacterial vaginitis, urethritis, bacterial conjunctivitis, chancroid, otitis media, chronic gastritis, peptic ulcer, diarrhea, Legionnaires' disease, leptospirosis, gonorrhea, arthritis, periodontal disease, salmonellosis, typhoid fever, shigellosis, rat bite fever, pharyngitis, scarlet fever, syphilis, cholera, Asiatic cholera, Yersina arthritis, bubonic plague, chronic pulmonary disease, Hansen's disease, leprosy, tuberculosis, dermal tuberculosis, psittachosis, omithosis, conjunctivitis, trachoma, lymphogranuloma venereum, genital tract infections, Q fever, primary atypical pneumonia, rickettsial pox, typhus, epidemic typhus, Rocky Mountain spotted fever, tsutsugamushi fever, nongonococcal urethritis, human erlichiosis, meningococcal meningitis, skin infections, corneal infections, external ear infections, candidiasis, monoiliasis, thrush, candidosis, mucositis, bacteremia, hepatitis, hepatitis A, hepatitis B, hepatitis C, hepatitis E, coccidiomycosis, lymphadenitis, balantidiasis cryptosporidosis, amoebiasis, amoebic dysentery, giardiasis, giardia enteritis, leishmaniasis, Kala-azar, malaria, toxoplasmosis, trypanosomiasis, Chagas disease, African sleeping sickness, dengue, Japanese encephalitis, Rift Valley fever, Ebola hemorrhagic fever, Venezuelan hemorrhagic fever, hantavirus pulmonary syndrome, hemorrhagic fever with renal syndrome, cytomegalovirus infection, poliomyelitis, West Nile virus disease, influenza, measles, condyloma, encephalitis, ankylosing spondylitis, arteritis, inflammatory bowel disease, polyarteritis nodosa, rheumatic fever, systemic Lupus erythematosus, Alzheimer's disease, multiple sclerosis, osteoporosis, Crohn's disease, strep throat, yellow fever, eczema, psoriasis, dermatitis, disease-induced skin ulcers, undefined tropical diseases, shingles, rashes, heat rashes, bedsores, cold sores, blisters, boils, herpes simplex, acne, pimples, skin chafing, skin cracking, itchiness, skin peeling, warts, one or more symptoms thereof, or any combination thereof. In another embodiment, the condition includes HIV (AIDS), or one or more symptoms. It should be understood that the invention includes the use of the compounds or compositions to prevent, treat, or manage each of these conditions individually or multiple conditions concurrently or sequentially. Thus, the prevention, treatment, or management of each condition should be understood as a separate embodiment.

The pathogens which may be killed by, or the growth or proliferation of which may be halted, diminished, or inhibited by, the electron active metal oxides of the present invention include, but are not limited to, gram-positive bacilli and cocci; gram-negative bacilli and cocci; acid-fast bacteria; other bacteria; fungi; parasitic microbes, e.g., protozoa; and viruses.

Examples of gram-positive bacilli and cocci include, but are not limited to, Actinomedurae, *Actinomyces israelii, Bacillus anthracis, Bacillus cereus, Clostridium botulinum, Clostridium difficile, Clostridium perfringens, Clostridium tetani,* Corynebacterium, *Enterococcus faecalis, Listeria monocytogenes,* Nocardia, *Propionibacterium acnes, Staphylococcus aureus, Staphylococcus epiderm, Streptococcus mutans, Streptococcus pneumoniae,* and combinations thereof.

Examples of gram-negative bacilli and cocci include, but are not limited to, *Afipia felis,* Bacteriodes, *Bartonella bacilliformis, Bortadella pertussis, Borrelia burgdorferi, Borrelia recurrentis,* Brucella, *Calymmatobacterium granulomatis,* Campylobacter, *Escherichia coli, Francisella tularensis, Gardnerella vaginalis, Haemophilius aegyptius, Haemophilius ducreyi, Haemophilius influenziae, Heliobacter pylori, Legionella pneumophila, Leptospira interrogans, Neisseria meningitidia, Porphyromonas gingivalis, Providencia sturti, Pseudomonas aeruginosa, Salmonella enteridis, Salmonella typhi, Serratia marcescens, Shigella boydii, Streptobacillus moniliformis, Streptococcus pyogenes, Treponema pallidum, Vibrio cholerae, Yersinia enterocolitica, Yersinia pestis,* and combinations thereof.

Examples of acid-fast bacteria include, but are not limited to, *Myobacterium avium, Myobacterium leprae, Myobacterium tuberculosis,* and combinations thereof.

Examples of other bacteria not falling into the other three categories include, but are not limited to, *Bartonella henseiae, Chlamydia psittaci, Chlamydia trachomatis, Coxiella burnetii, Mycoplasma pneumoniae, Rickettsia akari, Rickettsia prowazekii, Rickettsia rickettsii, Rickettsia tsutsugamushi, Rickettsia typhi, Ureaplasma urealyticum, Diplococcus pneumoniae, Ehrlichia chafensis, Enterococcus faecium,* Meningococci, and combinations thereof.

Examples of fungi include, but are not limited to, Aspergilli, Candidae, *Candida albicans, Coccidioides immitis,* Cryptococci, and combinations thereof.

Examples of parasitic microbes include, but are not limited to, *Balantidium coli, Cryptosporidium parvum, Cyclospora cayatanensis,* Encephalitozoa, *Entamoeba histolytica, Enterocytozoon bieneusi, Giardia lamblia,* Leishmaniae, Plasmodii, *Toxoplasma gondii,* Trypanosomae, trapezoidal amoeba, and combinations thereof.

Examples of viruses include, but are not limited to, Arboviruses, Ebola virus, Guanarito virus, Hanta virus, Hantaan virus, Hepatitis A, Hepatitis B, Hepatitis C, Hepatitis E, other Hepatitis viruses, Herpes-type viruses, Poliovirus, West Nile virus, Echo virus, and combinations thereof.

The antipathogenic or non-pathogenic compositions of the present invention may optionally further include the use of one or more additional therapeutic agents known to treat a condition, or a symptom thereof. Examples of such additional therapeutic agents include, but are not limited to, chelating agents, vitamins, minerals, silica hydride microclusters, analgesics, SambucolTM, aspirin, and the like.

The administration of one or more active ingredients and/or optional therapeutic agent(s), in accordance with the methods of the invention may occur together, concurrently but separately, sequentially, or a combination thereof. The optional additional therapeutic agent is generally a compound other than an electron active metal oxide compound.

The antipathogenic or antimicrobial performance of certain metal oxides may be improved or enhanced by the presence of an oxidizing agent. This is particularly the case when the metal oxide compounds or compositions are present in low amounts, i.e., typically less than 45 ppm, and more commonly when present in an amount less than about 40 ppm, based on the weight of the composition. In such situations, an oxidizing agent may be included in certain compositions of the invention in small amounts when the compositions are administered by certain routes. In such an embodiment, the oxidizing agent includes a peroxy acid salt, preferably a Group I salt of a persulfate, more preferably potassium persulfate. In another embodiment, the oxidizing agent includes the same peroxy acid salt which was present as a starting material in the reaction to form the particular electron active metal oxide. The oxidizing agent may advantageously be present in the composition in amounts from about 1 ppm to 500 ppm, based on the weight of the composition. In alternate embodiments, there may be from about 5 ppm to 200 ppm or from about 10 ppm to 100 ppm of oxidizing agent, based on the weight of the composition.

It is believed that the additional presence of certain types or amounts of oxidizing agent(s) may tend to irritate the skin, particularly when the compound or composition including metal oxide(s) is present in large amounts, such as greater than 50 ppm, based on the weight of the composition. In one embodiment, as more compound or composition is administered, a correspondingly smaller amount of undesirable oxidizing agent is required. Thus, in some embodiments, it has been found that the additional oxidizing agent is unnecessary and in fact undesirable for the purpose of treating certain conditions described herein, since the additional oxide may have or contribute to an undesirable side effect, for example, such as skin irritation when applied topically. For those embodiments, the compositions minimize the amount of additional oxidizing agent, such as persulfate, or are substantially or completely free of added persulfates or other oxidizing agents.

Certain of the electron active metal oxides may be black in color, such that care must be taken when formulating suitable topical pharmaceutical compositions according to the invention to inhibit blackening or superficial discoloration of the skin. Without being bound by theory, it is believed that larger amounts of such compositions promote increased superficial discoloration. Thus, in one embodiment, the pharmaceutical compositions preferably have an insufficient amount of metal oxide composition to cause visible skin discoloration.

Additionally, it was found by rigorous testing that certain silver tetroxide-containing compositions were comparatively non-toxic compared to silver salts, such as conventional formulations of silver nitrate, silver sulfadiazine, and benzoyl peroxide. Since these silver tetroxide compositions were effective at certain ppm concentrations in killing pathogens in nutrient broth and for water treatment, commercial concentrates were formulated with 2% of the tetrasilver tetroxide. For acceptance of the oxide in commerce, for which EPA registration No. 3432-64 was obtained, it was necessary for the $Ag_4O_4$ to undergo a series of toxicity tests. A 3% concentrate was used and evaluated by a certified laboratory employing good laboratory practice (GLP) according to the Code of Federal Regulations for this purpose. The results were as follows:

| Acute Oral Toxicity | $LD_{50}$ Greater than 5,000 mg/Kg |
|---|---|
| Acute Dermal Toxicity | $LD_{50}$ Greater than 2,000 mg/Kg |
| Primary Eye Irritation | Mildly irritating |
| Primary Skin Irritation | No irritation |
| Skin Sensitization | Non-Sensitizing |

Subsequent evaluations conducted according to the invention showed that unless persons were prone to silver allergies, the pure tetrasilver tetroxide compositions according to the invention could be applied to the skin without any ill effects or evidence of irritation, despite the fact that the compositions of the invention can be a powerful oxidizing agent.

Where the electron active compositions according to the invention are applied to the skin, they may be combined with a carrier in an amount from about 1 ppm to 500,000 ppm, more preferably from about 50 ppm to 250,000 ppm, of the electron active metal oxide composition, based on the weight of the composition. In various embodiments, the compositions are provided in amounts from about 100 ppm to 100,000 ppm, from about 500 ppm to 70,000 ppm, from about 5,000 ppm to 50,000 ppm, or from about 10,000 ppm to 40,000 ppm, based on the weight of the composition. In one preferred embodiment, the compositions are formulated with about 25,000 ppm to 35,000 ppm of metal oxide, based on the weight of the composition. It will be readily understood by those of ordinary skill in the art that the ppm concentration of electron active compound(s), such as metal oxide, in the composition is based on the total weight of the composition.

When treating or managing conditions that require skin growth, such as burn therapy or skin graft management or treatment, a preferred embodiment employs amounts of about 0.1 to 10 percent by weight, about 0.25 to 5 percent by weight, or about 2 to 4 percent by weight of the compounds or compositions of the invention. The compositions, when applied topically, can be applied to the skin about 1 to 3 times per day until the condition is suitably cured or satisfactorily controlled. In one embodiment, the composition may generally be topically applied at a dosage level of from about 1 mg to 1000 mg per $cm^2$ of skin surface, preferably about 10 mg to 500 mg per $cm^2$ of skin surface. When applied topically, a preferred carrier includes petroleum jelly, such as white petroleum jelly. For example, a suitable white petroleum jelly is available from Penreco of Houston, Tex.

Most of the metal oxide compounds, for example, for use according to the invention are commercially available from various sources. Tetrasilver tetroxide compositions for use according to the invention have been commercially sold under the poorly named "Ag(II) OXIDE" tradename. They may be obtained from Aldrich Chemical Co., Inc., having a place of business in Milwaukee, Wis. The chemical synthesis of tetrasilver tetroxide compounds can also be performed according to the method described on page 148 in M. Antelman, "Anti-Pathogenic Multivalent Silver Molecular Semiconductors," *Precious Metals*, vol. 16:141–149 (1992)

by reacting silver nitrate with potassium peroxydisulfate according to the following equation in alkali solutions:

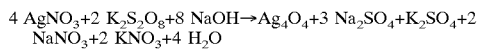

To the extent necessary to understand the present invention, the disclosure of Antelman is hereby incorporated herein by express reference thereto.

Tetracopper tetroxide, also referred to herein as Cu(I,III) oxide or $CU_4O_4$, may be prepared as follows.

Suitable copper-based starting materials for this reaction include at least one copper(I)-containing material. In one embodiment, a water soluble copper(I) salt can be used. Typically, a water soluble copper(I) salt can be prepared by dissolving an inorganic copper(I) compound, for example, such as cuprous oxide, in an appropriate acid, for example, an organic acid, such as acetic acid. Since soluble copper(I) salts are not readily commercially available at the present time, however, a non-solvated inorganic copper(I) compound, such as cuprous oxide itself, can be used as the copper(I)-containing starting material. In addition, other copper(I)-containing materials, either inorganic, such as a copper(I) oxide, or organic, such as an organometallic copper(I) compound, or both, may be used, where the copper(I)-containing material(s) are sufficiently soluble in an aqueous or organic solution to allow reaction with other materials to form an electron active copper oxide compound.

The copper(I)-containing starting material is combined with an aqueous caustic solution. This caustic solution preferably contains two components: a strong caustic base and a peroxy acid salt. Examples of suitable strong caustic bases include Group I and Group II hydroxides, preferably sodium hydroxide or potassium hydroxide. Examples of suitable peroxy acid salts include Group I salts of persulfates, preferably potassium persulfate.

The copper-based starting material is typically the limiting reagent in such a preparation. The ratio of each of the components in the caustic solution to that of the copper-based starting material is theoretically set by the stoichiometry of the particular reaction. In one preferred embodiment, there is a relative molar excess, i.e., an amount more than stoichiometrically necessary, of each of the components in the caustic solution with respect to the copper-based starting material. When a strong caustic base and a peroxy acid salt are present in the caustic solution, the relative molar excesses of the components may be at least about 50% and at least about 10%, respectively, preferably at least about 100% and at least about 20%, respectively, more preferably, at least about 250% and at least about 40%, respectively, most preferably at least about 500% and at least about 75%, respectively.

Generally, the reactants may be added together in any manner that comports with typical laboratory procedure. In one embodiment, the copper(I)-containing starting material is placed in a reactor, to which the strong caustic base and the peroxy acid salt are added, each typically in their own solutions. The solution containing the reactants is then typically heated to a temperature sufficient to activate a reaction, preferably sufficient to activate a reaction with no major undesirable side reactions or other undesirable effects, more preferably above about 80° C., most preferably about 90° C. to 95° C. The solution is heated for a time sufficient to facilitate the reaction, preferably to provide substantial completion of the reaction, preferably for at least about 5 minutes, more preferably for at least about 15 minutes, after which time the solution is allowed to cool or is cooled, preferably to below about 45° C., more preferably to about room temperature.

The color change of the solution, from its original color, red, to a color indicating a reaction has occurred, in this case black, may occur at the heated temperature or during or after cooling.

The purification and isolation of the desired product can be accomplished by any suitable method available to those of ordinary skill in the art. In the majority of situations, the desired reaction product is primarily a solid, but may be dissolved or dispersed in at least part of the solution. In one preferred embodiment, the solution is carefully decanted off, and then the remaining product is washed multiple times with distilled water, before being sufficiently dried. In another preferred embodiment, the solution is vacuum filtered to remove the filtrate, and the remaining product is sufficiently dried.

The yield of solid tetracopper tetroxide material, based on the reactants, is typically at least about 10%, preferably at least about 45%, more preferably at least about 75%, most preferably at least about 80%.

In addition, Fe(II,III) oxide and Mn(II,III) oxide are commercially available from Aldrich Company of Milwaukee, Wis., and Co(II,III) oxide and Pr(III,IV) oxide are commercially available from Noah Technologies of San Antonio, Tex. Also, Bi(III,V) oxide synthetic routes are detailed and reviewed in *Gmelins Handbuch Der Anorganischen Chemie*, vol. 16:642 (1964), and the oxide is available commercially from City Chemicals of New York, N.Y.

The magnitude of a prophylactic or therapeutic dose of electron active composition(s), or a derivative thereof, in the acute or chronic management of diseases and disorders described herein will vary with the severity of the condition to be prevented, treated, or managed and the route of administration. For example, oral, mucosal (including rectal and vaginal), parenteral (including subcutaneous, intramuscular, bolus injection, and intravenous, such as by infusion), sublingual, transdermal, nasal, buccal, and like may be employed. In one embodiment, a patient may gargle using the composition of the present invention. Dosage forms include tablets, troches, lozenges, dispersions, suspensions, suppositories, solutions, capsules, soft elastic gelatin capsules, patches, and the like. The dose, and perhaps the dose frequency, will also vary according to the age, body weight, and response of the individual patient. Suitable dosing regimens can be readily selected by those of ordinary skill in the art with due consideration of such factors. In general, the total daily dosage for the conditions described herein, is from about 0.1 mg to 1,000 mg of the active ingredient, i.e., one of the metal oxides described herein, or a derivative thereof. In another embodiment, the daily dosage can be from about 1 mg to 500 mg, while in another embodiment, the daily dosage can be from about 2 mg to 200 mg of the metal oxide composition. A unit dosage can include, for example, 30 mg, 60 mg, 90 mg, 120 mg, or 300 mg of metal oxide composition. Preferably, the active ingredient is administered in single or divided doses from one to four times a day, such as by topical administration. In another embodiment, the compositions are administered by an oral route of administration. The oral dosage forms may be conveniently presented in unit dosage forms and prepared by any methods available to those of ordinary skill in the art of pharmacy.

In managing the patient, the therapy may be initiated at a lower dose, e.g., from about 1 mg, and increased up to the recommended daily dose or higher depending on the patient's global response. It is further recommended that children, patients over 65 years, and those with impaired renal or hepatic function, initially receive low doses when administered systemically, and that they be titrated based on individual response(s) and blood level(s). It may be necessary to use dosages outside these ranges in some cases, as will be apparent to those of ordinary skill in the art. Furthermore, it is noted that the clinician or treating physician will know how and when to interrupt, adjust, or terminate therapy in conjunction with individual patient response.

Any suitable route of administration may be employed for providing the patient with an effective dosage of electron active metal oxide, or a derivative thereof. The most suitable route in any given case will depend on the nature and severity of the condition being prevented, treated, or managed. In one embodiment where burns or skin grafts are being treated or managed, the compounds or compositions may be administered topically.

In practical use, the electron active compound, such as a metal oxide, or a derivative thereof, can be combined as the active ingredient in intimate admixture with a pharmaceutical carrier medium according to conventional pharmaceutical compounding techniques. The carrier may take a wide variety of forms and may include a number of components depending on the form of preparation desired for administration. The compositions of the present invention may include, but are not limited to, suspensions, solutions and elixirs; aerosols; or carriers, including, but not limited to, starches, sugars, microcrystalline cellulose, diluents, granulating agents, lubricants, binders, disintegrating agents, and the like.

Suitable forms in which the electron active compounds or compositions of the present invention may be used include, but are not limited to, powder, granule, flake, solution, suspension, emulsion, slurry, aerosol spray, gel, paste, and combinations thereof. In one preferred embodiment, the form is a powder or solution. When the electron active compounds are in the form of a solution, the solution may be aqueous, non-aqueous, or a combination thereof, preferably at least partially aqueous, more preferably substantially aqueous. In a preferred embodiment, the metal oxides are in an aqueous solution.

The compositions of the invention may be applied topically, e.g., either directly as a powder, powder crystals, or granules, or in other non-sprayable or sprayable forms. Non-sprayable forms can be semi-solid or solid forms including a carrier indigenous to topical application and preferably having a dynamic viscosity greater than that of water. Suitable formulations include, but are not limited to, suspensions, emulsions, creams, ointments, powders, liniments, salves and the like. If desired, these may be sterilized or mixed with any available auxiliary agents, carriers, or excipients, e.g., thixotropes, stabilizers, wetting agents, and the like. One or more thixotropic agents can be included in types and amounts sufficient to increase adhesion of topically applied compositions of the invention to the skin, so as to inhibit or prevent runoff or other loss of the composition from the treatment zone on the skin. Preferred vehicles for non-sprayable topical preparations include ointment bases, e.g., polyethylene glycol-1000 (PEG-1000); conventional ophthalmic vehicles; creams; and gels, as well as petroleum jelly and the like. In one more preferred embodiment, the carrier includes a petroleum jelly. In another preferred embodiment, the carrier is formulated as a cream, gel, or lotion. In another preferred embodiment, the carrier is 3 weight percent active ingredient, 36 weight percent heavy mineral oil, 47 weight percent petroleum jelly, and 14 weight percent Tivawax P, which is available from Tivian Laboratories, Inc., of Providence, R.I. In yet another preferred embodiment, the composition may be a dry powder, such as with 5 weight percent active ingredient and 95 weight percent bismuth subgallate. These topical preparations may also contain emollients, perfumes, and/or pigments to enhance their acceptability for various usages.

The compositions may also be formulated for parenteral administration by injection (subcutaneous, bolus injection, intramuscular, or intravenous, such as by infusion), and may be dispensed in a unit dosage form, such as a multidose container or an ampule. Compositions of the electron active metal oxide, or a derivative thereof, for parenteral administration may be in the form of suspensions, solutions, emulsions, or the like, in aqueous or oily vehicles, and in addition to the active ingredient, may contain one or more formulary agents, such as dispersing agents, suspending agents, stabilizing agents, preservatives, and the like.

In the case where an intravenous injection or infusion composition is employed, a suitable dosage range can be, e.g., from about 0.5 mg (0.1 ppm) to about 1,000 mg (200 ppm) total dose, preferably from about 5 mg (1 ppm) to 400 mg (80 ppm). In one preferred embodiment, the total dose can be from about 50 mg (10 ppm) to 200 mg (40 ppm). It should be understood that any suitable amount of the composition according to the invention may be administered if effective to prevent, treat, or manage one or more conditions described herein.

Pharmaceutical compositions of the present invention may be orally administered in discrete pharmaceutical unit dosage forms, such as capsules, cachets, soft elastic gelatin capsules, tablets, or aerosols sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the pharmaceutically acceptable carrier which constitutes one or more necessary ingredients. In general, the compositions are prepared by uniformly and intimately admixing the active ingredient with liquid carriers or finely divided solid carriers or both, and then, if necessary, shaping the product into the desired presentation. Suitable types of oral administration include oral solid preparations, such as capsules or tablets, or oral liquid preparations. If desired, tablets may be coated by standard aqueous or nonaqueous techniques.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, granulating agent, surface active agent, dispersing agent, or the like. Molded tablets may be made by molding, in a suitable machine, a mixture of the powdered compound moistened with an inert liquid diluent. In one embodiment, each tablet, capsule, cachet, or gel cap contains from about 0.5 mg to about 500 mg of the active ingredient, while in another embodiment, each tablet contains from about 1 mg to about 250 mg of the active ingredient. The amount of active ingredient found in the composition, however, may vary depending on the amount of active ingredient to be administered to the patient.

The electron active compound(s), or a derivative thereof, may be formulated as a pharmaceutical composition in a soft elastic gelatin capsule unit dosage form by using conventional methods well known in the art, such as in Ebert, *Pharm. Tech*, 1(5):44–50 (1977). Soft elastic gelatin capsules have a soft, globular gelatin shell somewhat thicker than that of hard gelatin capsules, wherein a gelatin is plasticized by the addition of plasticizing agent, e.g., glycerin, sorbitol, or a similar polyol. The hardness of the capsule shell may be changed by varying the type of gelatin used and the amounts of plasticizer and water. The soft gelatin shells may contain an additional preservative, such as methyl- and propylparabens and sorbic acid, to prevent the growth of fungi, although this is not essential since the compounds and compositions of the invention provide antifungal efficacy. Thus, in one embodiment, the invention includes a compositions formulated as a gelatin shell with the composition of the invention, e.g.,a metal oxide, completely free of added preservatives. The active ingredient may be dissolved or suspended in a liquid vehicle or carrier, such as vegetable or mineral oils, triglycerides, surfactants such as polysorbates, or a combination thereof.

In addition to the common dosage forms set out above, the compounds of the present invention may also be administered by controlled release means, delivery devices, or both, as are well known to those of ordinary skill in the art, such as those described in U.S. Pat. Nos.: 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, the disclosures of which are hereby incorporated herein by express reference thereto. These pharmaceutical compositions can be used to provide slow or controlled-release of the active ingredient therein using, for example, hydropropylmethyl cellulose in varying proportions to provide the desired release profile, other polymer matrices, gels, permeable membranes, osmotic systems, multilayer coatings, microparticles, liposomes, microspheres, or the like, or a combination thereof. Suitable controlled-release formulations available to those of ordinary skill in the art, including those described herein, may be readily selected for use with the compositions of the invention. Thus, single unit dosage forms suitable for topical or oral administration, such as gels, lotions, cremes, tablets, capsules, gelcaps, caplets, and the like, that are adapted for controlled-release are encompassed by the present invention.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations may include: 1) extended activity of the drug; 2) reduced dosage frequency; and 3) increased patient compliance.

Most controlled-release formulations are designed to initially release an amount of drug that promptly produces the desired therapeutic effect, and gradual and continual release of other amounts of drug to maintain this level of therapeutic effect over an extended period of time. In order to maintain this constant level of drug in the body, the drug should be released from the dosage form at a rate that will replace the amount of drug being metabolized and excreted from the body.

The controlled-release of the active ingredient may be stimulated by various inducers, for example pH, temperature, enzymes, water, or other physiological conditions or compounds. The term "controlled-release component" in the context of the present invention is defined herein as a compound or compounds, including polymers, polymer matrices, gels, permeable membranes, liposomes, microspheres, or the like, or a combination thereof, that facilitates the controlled-release of the active ingredient (e.g., tetrasilver tetroxide or another metal oxide) in the pharmaceutical composition.

The skin-growth-enhancing compositions for use in the present invention include electron active metal oxides, or a derivative thereof, as the active ingredient, and may also contain a pharmaceutically acceptable carrier, and optionally, other therapeutic ingredients. Suitable derivatives include any available "pharmaceutically acceptable salts," which refer to a salt prepared from pharmaceutically acceptable non-toxic acids including inorganic acids, organic acids, solvates, hydrates, or clathrates thereof. Examples of such inorganic acids are nitric, sulfuric, lactic, glycolic, salicylic, and phosphoric. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Particularly preferred acids are lactic, glycolic, and salicylic acids. The pharmaceutically acceptable salts preferably do not include halide-containing salts when tetrasilver tetroxide is present, as these salts are believed to facilitate breakdown of the oxide lattice present in the silver oxide compositions of the invention.

EXAMPLES

These and other aspects of the present invention may be more fully understood with reference to the following non-limiting examples, which are merely illustrative of the preferred embodiment of the present invention, and are not to be construed as limiting the invention, the scope of which is defined by the appended claims.

Example 1

Method of Treating Diabetes-Induced Foot Ulcers According to Invention

Twenty eight patients in the age group ranging from 45 to 65 having diabetes-induced foot ulcers were arranged in two groups. All of the patients were taking insulin injections and were diagnosed as Type I insulin dependent. Moreover, all of the patients had presented the diabetic foot condition for at least 10 days prior to treatment Group I included fourteen patients where culture swabs of the ulcerated skin indicated the presence of bacteria (infection). Group II included fourteen patients where culture swabs of the ulcerated skin did not indicate the presence of abnormal amounts of bacteria (no infection).

The patients in each group were treated by applying 200 mg of a petroleum jelly containing 3 wt % tetrasilver tetroxide twice daily to the ulcerated sores for a 30-day period. Daily evaluations of the skin condition were conducted by a dermatologist.

Summary of Results

Group I: Within 48 hours of the onset of treatment, the sores on the feet of all patients began to dry out. After 72 hours, the ulcers on all patients started to heal at the borders. By the fourth day, inflammation of the diseased tissue eased, and by the sixth day the ulcers were completely dry with no surface secretions. By the tenth day, the ulcers on all patients feet had completely disappeared. Lab tests indicated no sign of infection on the feet of any patient by the tenth day.

Group II: Within 24 hours of the onset of treatment the sores on the feet of all patients began to dry out and heal at the borders with no secretion. By the third day, the sores on all patients were covered with new healthy tissue. By the tenth day, the ulcers had healed and completed the process of forming scar tissue by 80%. At day 14 of the treatment, all of the ulcers were 100% healed with no sign of infection.

Continuous monitoring of both groups over the 30-day period indicated no reappearance of the ulcers.

The above tests demonstrated that tetrasilver tetroxide treatment was effective in both curing infections associated with diabetes-induced ulcers and healing the ulcers themselves. Without being bound by theory, it is believed that the active tetroxide compositions of the present invention accelerated the neovascularization process of the affected tissue and facilitated the treatment.

Example 2

Effect of Compositions of Invention on Burn Therapy

Fourteen (14) patients ranging in age from 11 to 38 years old were diagnosed as having tissue injury caused by thermal contact. These patients were arranged in two groups, and all previous treatments were removed before any new treatments were applied.

Group I: 7 patients were diagnosed as having second degree burns, 20% BSA, of moderate severity on the hands and arms. These patients had received anterior treatment for one week. The conventional anterior treatment was a standard burn therapy composition including 0.5 weight percent of silver nitrate solution, mafenidate acetate, and 1 percent silver sulfadiazine. All patients presented bacterial invasion including streptococci and staphylococci. The tissue on all patients had blisters and fibrinous exudate. Each patient applied 200 mg of ointment containing 3 wt % tetrasilver tetroxide in 97 wt % petroleum jelly three times daily to the arm burns, which were then covered by 3 layers of cotton roll bandages. The hands of each was covered by gloves, which were changed every 10 days, that contained 500 mg of ointment (3 wt % tetrasilver tetroxide and 97 wt % petroleum jelly). The patients were evaluated every day for 30 days in the hospital, without any outpatient treatment and with daily laboratory tests.

Group II: The other 7 patients were diagnosed as having third degree burns, 40% to 65% BSA, large severity, on both hands, arms, feet, and legs. All members received the same conventional anterior treatment as the Group I patients.

Group IIA: Four of these patients had 40% BSA burns with lab results showing no bacterial invasion. These patients had normal temperature curves and hemograms, and they had skin surfaces that were pale and anesthetic. These patients received electrolyte volume replacement. They each applied 300 mg of the same ointment noted above 3 times per day for 30 days, with hands in gloves containing 500 mg of the same ointment and changed every ten days. Laboratory tests were performed every week.

Group IIB: Three of the patients had 65% BSA burns with bacterial invasion confirmed by lab testing. The temperature curve of each was in the range of 39.5° C. to 39.9° C. at the beginning of treatment. The hemograms of each showed a marked leucositosis, and the skin surfaces were black, charred, and leathery. All patients in this group had escharotomies before treatment and the fever did not disappear. This group received the same treatment as Group IIA above.

Results

Group I: Over a period of 6 to 9 days, all patients observed the burn lesions dry out, and all blisters and erythematous areas disappear. Minimal fibrinous exudate was present, with no patient having a fever. By day 14, the hemograms became normal. In 10 more days, i.e., by day 24, the lesions in the hands were evaluated. The skin was completely healed and had no more fibrinous exudate. Skin cultures were normal with no bacterial invasion reported. Skin necrosis did not develop in any patient in this group, and all joint functions were preserved. None of the patients had to be in a surgery room for wound cleaning, removal, or debridement. Even after six months of conventional treatment, the results do not match those after 30 days of treatment using the compositions and methods of the present invention.

Group IIA: At day 10, the gloves were removed from all patients and the skin of the hands was healed with no sign of skin necrosis. All joint functions were preserved and no patient had wound bed contractions. Escharotomies were not required, and none of the patients developed sodium loss, hypokalemia, hypochloremia, alkalosis, or methemoglobinuria, each of which is an adverse effect that may occur in burn victims during or following conventional treatment. Over a period of 13 to 20 days, all patients in this group had the injured skin become normal in color and texture. No bacterial invasion was present after the treatment and lab tests were normal.

Group IIB: At day 10, the gloves were removed from all patients and the skin of the hands was healed about 50%. At day 20, the gloves were removed again and the injured skin was all healed with no sign of skin necrosis. All of the skin on the patients developed wound bed contractions, but all joint functions were preserved. About one-third of the patients developed sodium loss and hypokalemia, but none developed hypochloremia, alkalosis, or methemoglobinuria. Over a period of 23 to 28 days, the injured skin on all patients in this group dried out and lab tests did not indicate the presence of bacterial invasion. No fever was present and the black, charred, leathery skin became normal skin. The patients of this group continued with outpatient follow-up to evaluate the wound bed contractions, examine the skin for cellulitis, and to consider excisional therapy.

Conclusions

The composition according to the invention used for treating second degree burns, 20% BSA, of moderate severity with bacterial invasion seemed to eliminate 100% of the bacteria and heal the injured skin in a record time of 10 days. The use of gloves filled with a composition prepared according to the invention to treat hand burns healed these burns faster than any known conventional hand burn treatment. The composition of the invention also prevented bacterial invasion of skin burn injury having no bacterial invasion, prevented skin necrosis in burn injuries, and increased the speed of healing of tissue caused by thermal burn contact. With respect to third degree burns, the composition of the invention caused sodium losses and hypokalemia, but helped to preserve joint functions.

Example 3

Compositions of Invention Compared to Art

A comparison study was conducted of tetrasilver tetroxide, prepared in accordance with the present invention, and a conventional monovalent silver oxide. Benchmark Analytics of Center Valley Pa., a licensed certifying laboratory, tested the efficacy of 2 ppm of each compound against *E. Coli*. A 100,000 CFU/mL culture had a 43% kill, i.e., of 43,000 in 10 minutes contact time with the composition of the invention, compared with a 37.3% reduction with the conventional silver oxide of a 75,000 CFU/mL culture under the same conditions. Since the tetrasilver tetroxide contains 87% silver by weight, and the conventional silver oxide contains 93% silver by weight, the silver does not appear to be primarily responsible for the antimicrobial efficacy of the composition of the invention. Indeed, when one adjusts the results to a content of 2 ppm silver, the tetrasilver tetroxide kills 49,000, and the conventional compound kills only 30,000, each calculated for a 100,000 CFU/mL culture, of *E. Coli*. Thus, the antibacterial efficacy of the composition of the invention is believed to facilitate the treatment or management of burns. In one embodiment, the electron active compound can inhibit or prevent bacterial or other pathogenic invasion of burns or skin grafts, which can facilitate healing.

Based on all of the test data described above, the healing mechanism associated with the use of the metal oxides of the invention to treat and manage at least some skin diseases, without being bound by theory, appears to involve mechanisms other than merely inhibiting or killing pathogens and curing infections that tend to aggravate disease and retard the natural healing process. The data indicate that healing is brought about even in cases where no abnormal bacteria counts or infection is evident. This suggests that the electron active compound(s) may also act against auto-antibodies that trigger autoimmune reactions associated with diseased tissue, as well as against other non-pathogenic conditions or diseases, such as circulatory or neurological conditions or diseases.

Although preferred embodiments of the invention have been described in the foregoing Detailed Description, it will be understood that the invention is not limited to the embodiments disclosed, but is capable of numerous rearrangements and modifications of parts and elements without departing from the spirit of the invention. It will be further understood that the chemical and pharmaceutical details of the compositions and methods of prevention, treatment, or management herein may be slightly different or modified by one of ordinary skill in the art without departing from the claimed invention.

What is claimed is:

1. A method for facilitating or enhancing growth of a patient's skin, which comprises administering at least one electron active compound that has at least two polyvalent cations, at least one of which has a first valence state and at least one of which has a second different valence state, said at least one electron active compound being administered in an amount and for a period of time which is therapeutically effective to facilitate or enhance skin growth, and wherein the electron active compound comprises at least one of Bi(III,V) oxide, Co(II,III) oxide, Cu(I,III) oxide, Fe(II,III) oxide, Mn(II,III) oxide, or Pr(III,IV) oxide.

2. The method of claim 1, wherein the patient is a mammal and wherein the therapeutically effective amount of the electron active compound(s) administered is from about 1 ppm to 500,000 ppm.

3. The method of claim 2, wherein the therapeutically effective amount is from about 50 ppm to 100,000 ppm.

4. The method of claim 2, wherein the mammal is a human and wherein the at least one electron active compound is administered topically or transdermally.

5. The method of claim 1, wherein the method further comprises administering at least one additional different therapeutic agent present in an amount sufficient to facilitate or enhance growth of the patient's skin and wherein the at least one additional therapeutic agent comprises at least one of a chelating agent, a vitamin, a mineral, silica hydride microclusters, an analgesic, elderberry extract, and aspirin.

6. The method of claim 5, wherein the at least one additional therapeutic agent is administered concurrently with the at least one electron active metal oxide compound.

7. The method of claim 1, further which comprises combining the at least one electron active compound with a carrier medium before administration to the patient, wherein the carrier medium comprises petroleum jelly or a thixotropic agent sufficient to increase adherence of the composition to the skin without excessive runoff.

8. The method of claim 1, wherein the composition is administered topically directly to the skin in the form of a powder.

9. The method of claim 1, wherein the administering comprises application of the at least one electron active compound to the skin at a dosage level of about 10 mg to 500 mg per $cm_2$ of skin surface.

10. The method of claim 1, wherein the amount is insufficient to cause adverse effects.

11. The method of claim 1, wherein the facilitating or enhancing of skin growth comprises the treatment or management of a burn or skin graft, or a symptom thereof.

12. A skin-growth-enhancing composition comprising:
   (a) a therapeutically effective amount of at least one electron active compound that has at least two polyvalent cations, at least one of which has a first valence state and at least one of which has a second different valence state, the at least one electron active compound being present in an amount which is therapeutically effective to facilitate or enhance skin growth, and wherein the electron active compound comprises at least one of Bi(III,V) oxide, Co(I,III) oxide, Cu(II,III) oxide, or Pr(III,IV) oxide; and
   (b) a carrier comprising at least one of a petroleum jelly or a thixotropic agent present in an amount sufficient to increase adherence of the composition to skin without excessive runoff.

13. The skin-growth-enhancing composition of claim 12, wherein the at least one electron active compound is present in an amount of from about 1 ppm to 500,000 ppm.

14. The skin-growth-enhancing composition of claim 12, in the form of a powder, or a plurality of powder crystals or granules.

15. The skin-growth-enhancing composition of claim 12, further comprising an oxidizing agent present in an amount sufficient to enhance efficacy of the active compound but insufficient to cause skin irritation.

16. A wound dressing comprising the composition of claim 12.

17. The wound dressing of claim 16, wherein the wound dressing comprises an adhesive-containing bandage, a cotton roll bandage, or a gellable polymer.

18. A dressing comprising at least one electron active compound, the electron active compound having at least two polyvalent cations, at least one of which has a first valence state and at least one of which has a second different valence state, wherein the electron active compound comprises at least one of Bi(III,V) oxide, Co(II,III) oxide, Cu(I,III) oxide, Mn(II,III) oxide, or Pr(III,IV) oxide.

19. The dressing of claim 18, wherein the dressing comprises a therapeutically sufficient amount of the electron active compound to manage, or treat at least one of wound, a burn, a lesion, an ulcer, a sore, a boil, a wart, or combination thereof.

20. The dressing according to claim 18, further comprising an oxidizing agent present in an amount sufficient to enhance efficacy of the electron active compound but insufficient to cause skin irritation.

21. The dressing according to claim 18, wherein the dressing comprises at least one of a bandage or a gellable polymer.

22. The dressing according to claim 18, wherein the electron active compound is in the form of a powder, a plurality of powder crystals, granules, or combination thereof.

23. A method treating or managing one or more conditions, which comprises topically administering to a patient at least one dressing comprising at least one electron active compound, the electron active compound having at least two polyvalent cations, at least one of which has a first valence state and at least one of which has a second different valence state, wherein the electron active compound comprises at least one of Bi(III,V) oxide, Co(II,III) oxide, Cu(I,III) oxide, Mn(II,III) oxide, or Pr(III,IV) oxide, and wherein the condition comprises at least one of a wound, a burn, a lesion, an ulcer, a sore, a boil, a wart, or combination thereof.

24. The method according to claim 23, wherein each electron active compound is present in a therapeutically effective amount.

25. The method of claim 23, wherein the dressing comprises at least one of a bandage or a gellable polymer.

* * * * *